United States Patent
Li et al.

(10) Patent No.: US 11,369,702 B2
(45) Date of Patent: Jun. 28, 2022

(54) KITS AND METHODS FOR PREPARING RADIOPHARMACEUTICALS

(71) Applicant: Institute of Nuclear Energy Research, Atomic Energy Council, Executive Yuan, R.O.C, Taoyuan (TW)

(72) Inventors: Ming-Hsin Li, Taoyuan (TW);
Shih-Wei Lo, Taoyuan (TW);
Sheng-Nan Lo, Taoyuan (TW);
Shih-Ying Lee, Taoyuan (TW);
Su-Jung Chen, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 196 days.

(21) Appl. No.: 16/910,264

(22) Filed: Jun. 24, 2020

(65) Prior Publication Data
US 2021/0369878 A1    Dec. 2, 2021

(30) Foreign Application Priority Data
May 26, 2020 (TW) ................................ 109117466

(51) Int. Cl.
*B01J 19/00* (2006.01)
*A61K 51/12* (2006.01)

(52) U.S. Cl.
CPC ......... *A61K 51/1282* (2013.01); *B01J 19/004* (2013.01)

(58) Field of Classification Search
CPC .............................. A61K 51/1282; B01J 19/00
See application file for complete search history.

(56) References Cited

PUBLICATIONS

Fei Liu et al., 68Ga/177Lu-labeled DOTA-TATE shows similar imaging and biodistribution in neuroendocrine tumor model, Tumor Biology, 1-9. (Year: 2017).*

* cited by examiner

*Primary Examiner* — Michael G. Hartley
*Assistant Examiner* — Jagadishwar R Samala
(74) *Attorney, Agent, or Firm* — Locke Lord LLP; Tim Tingkang Xia, Esq.

(57) ABSTRACT

Disclosed herein are kits and methods for preparing radiopharmaceuticals. The kits and methods of the present disclosure can prepare the radiopharmaceuticals without using a heater and computer monitoring equipment. The kit includes a frozen crystal reaction vial, a reagent vial and a labeling holder, wherein the labeling holder contains a heating bag that can heat up to a high temperature of at least 95° C. by adding an aqueous solution.

9 Claims, 3 Drawing Sheets

KITS AND METHODS FOR PREPARING RADIOPHARMACEUTICALS

CROSS-REFERENCE TO RELATED APPLICATION

This application claims priority to Taiwan patent application No. TW109117466 filed on May 26, 2020, which is hereby incorporated by reference in its entirety.

TECHNICAL FIELD

The present invention relates to the field of medical radiography and therapy, in particular to kits and methods for rapidly preparing radiopharmaceuticals.

BACKGROUND

In existing methods of radiolabeling peptides/compounds, no matter manual operations or full-automatic operations, in order to maintain stable heating, a plug-in dry bath heater is still required for reaction heating mainly in the process of the step of labeling a radioactive nuclide, and the preparation process is cumbersome, so that in the clinical radiography or therapy process, there are restrictions on radiopharmaceutical preparation by medical personnel, and the radiopharmaceuticals cannot be provided in real time.

Therefore, there is an urgent need in the field for a kit and method for preparing radiopharmaceuticals so as to overcome the defects of the related art.

SUMMARY

In order to make readers understand the basic meaning of the disclosed content, the content of the present invention provides brief descriptions of the disclosed content. The content of the present invention is not a complete description of the disclosed content, and it is not intended to define the technical features or the scope of rights of the present invention.

One pattern of the present invention relates to a kit for preparing radiopharmaceuticals. The kit comprises a frozen crystal reaction vial comprising a peptide pharmaceutical, gentisic acid and mannitol configured to be mixed with a radioactive nuclide; a reagent vial comprising a buffer solution configured to be added into the frozen crystal reaction vial; and a labeling holder comprising a tank body, a heating area, a heating bag, a bearing seat, and an upper cover. The heating area is arranged at a bottom of the tank body. The heating bag is arranged in the heating area and is capable of heating up to at least 95° C. by adding an aqueous solution. The bearing seat is arranged above the heating area and configured to bear the frozen crystal reaction vial. The upper cover is arranged above the tank body. In an implementation, at least one air hole is formed in the upper cover.

According to an implementation of the present invention, the heating bag in the kit mainly has aluminum powder, calcium oxide, sodium carbonate and sodium hydroxide. According to a relatively specific implementation, the heating bag in the kit mainly has 15 to 20 wt % of aluminum powder, 50 to 60 wt % of calcium oxide, 20 to 25 wt % of sodium carbonate and 20 to 25 wt % of sodium hydroxide.

In an implementation, the kit further comprises a filter, configured to be inserted onto the frozen crystal reaction vial.

The other pattern of the present invention relates to a method for preparing radiopharmaceuticals through the kit according to any one of the above implementations, comprising the following steps:

(1) adding a radioactive nuclide and a buffer solution in a reagent vial into a frozen crystal reaction vial and performing mixing;

(2) adding an aqueous solution into a heating area to heat up a heating bag; and (3) placing the frozen crystal reaction vial on a bearing seat to perform a heating reaction, so as to obtain the radiopharmaceuticals.

In optional implementations, a peptide pharmaceutical is DOTATATE, DOTATOC, DOTANOC or DOTAOC, and the radioactive nuclide is Ga-68 or Lu-177. In addition, when the radioactive nuclide is the Ga-68, the buffer solution is an acetate buffer solution. When the radioactive nuclide is the Lu-177, the buffer solution is an ascorbic acid buffer solution. Furthermore, in other implementations, the heating reaction is at a temperature of at least 95° C. for at least 5 minutes.

A person of ordinary skill in the art to which the present invention belongs may fully understand the central concept of the present invention, the technical means adopted, and various implementation aspects after referring to the following implementations.

BRIEF DESCRIPTION OF THE DRAWINGS

To make the foregoing and other objectives, features, advantages, and embodiments of the present invention more comprehensible, descriptions of the drawings are as follows.

DETAILED DESCRIPTION

To make the description of the present invention more detailed and complete, the following provides an illustrative text description of the implementation aspects and specific embodiments of the present invention. However, the implementation aspects and specific embodiments of the present invention are not limited thereto.

Unless otherwise stated, the scientific and technical terms used in this specification have the same meanings as those understood and used by a person of ordinary skill in the art. In addition, a noun used in this specification covers the singular and plural forms of the noun unless otherwise specified.

As described in this specification, the term "about" generally means that an actual value falls within plus or minus 10%, 5%, 1%, or 0.5% of a specific value or range. The term "about" in this specification means that an actual value falls within an acceptable standard error of an average value, depending on the consideration of a person of ordinary skill in the art to which the present invention belongs. Except for experiment examples, or unless otherwise clearly stated, it should be understood that the ranges, numbers, values, and percentages used herein are all modified by "about". Therefore, unless otherwise stated, the values or parameters disclosed in this specification and the appended claims are all approximate values, and may be changed as required.

The term "peptide pharmaceutical" herein is a peptide pharmaceutical available in the current market. In an implementation of the present invention, the "peptide pharmaceutical" refers to a peptide pharmaceutical with a chelating agent DOTA, such as DOTATATE, DOTATOC, DOTANOC or DOTAOC.

In order to solve the problem existing in the related art, the present invention provides a novel kit and method for rapidly preparing radiopharmaceuticals. Specifically, by utilizing the kit of the present invention, radiolabeling can be rapidly completed without other heating equipment. The kit is quite convenient to use, is not limited by laboratory equipment and the environment, and is more convenient in clinical application.

Figure 1:
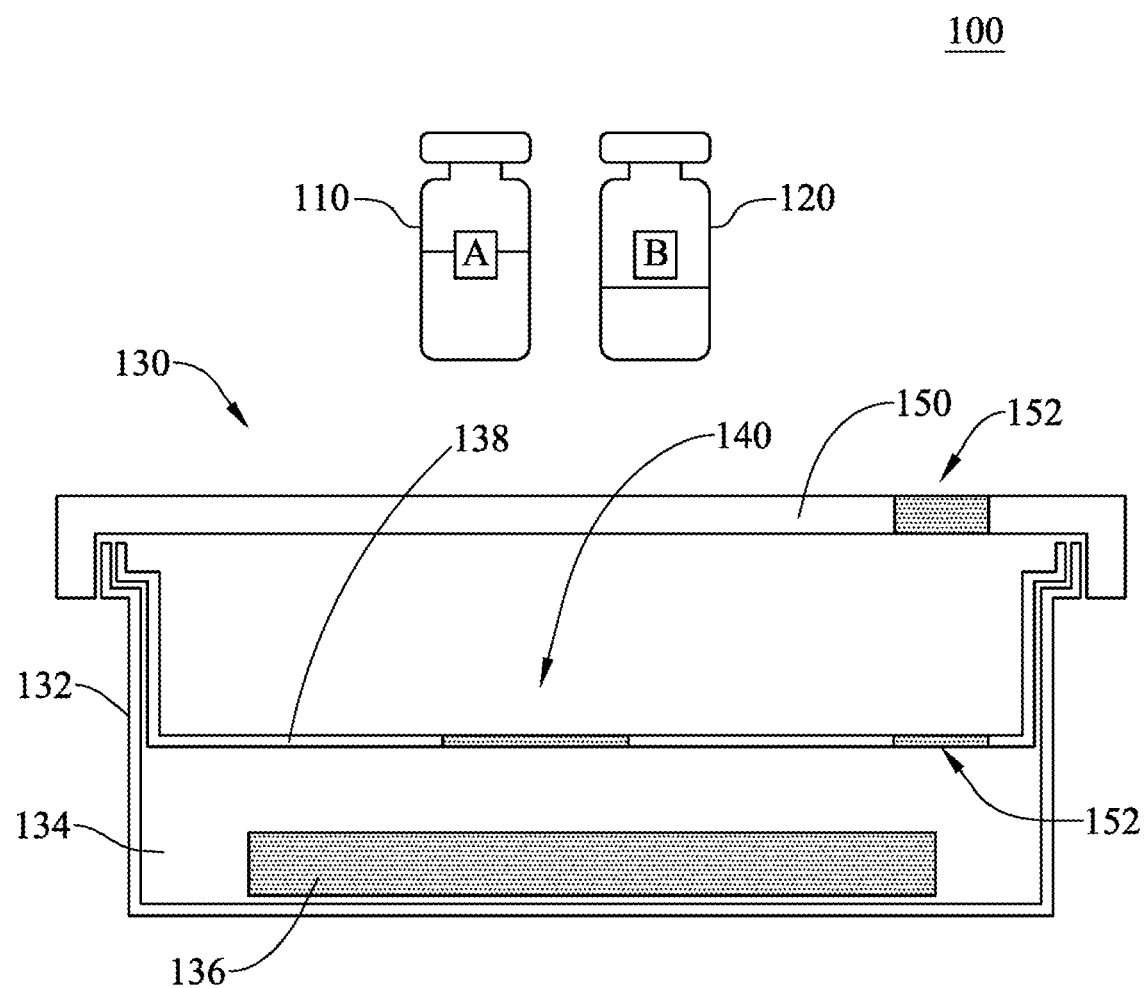
FIG. 1 is a kit for preparing radiopharmaceuticals according to an implementation of the present invention.

FIG. 1 is a kit 100 for preparing radiopharmaceuticals according to an implementation of the present invention.

In a specific implementation, the kit of the present invention includes a frozen crystal reaction vial 110, a reagent vial 120 and a labeling holder 130. The frozen crystal reaction vial 110 includes a freeze-dried peptide pharmaceutical, gentisic acid and mannitol. The reagent vial 120 includes a buffer solution suitable for radiolabeling. The frozen crystal reaction vial 110 or the reagent vial 120 may be vials, tubes, bottles and other similars. The labeling holder 130 is a sealed container capable of being opened and closed so that pollution can be avoided in the operating process, and for a specific structure of the labeling holder, reference may be made to FIG. 1. The labeling holder 130 includes a tank body 132 configured to provide a space for performing a reaction, a heating area 134 arranged at a bottom of the tank body 132, a heating bag 136 arranged in the heating area 134, a bearing seat 138 arranged above the heating area 134 and configured to bear the frozen crystal reaction vial 110, and an upper cover 150 covering an upper part of the tank body 132. In the present implementation, a bearing hole 140 is formed in the bearing seat 138 and configured to allow the frozen crystal reaction vial 110 to penetrate and be clamped in the bearing hole 140, so that a vial bottom and the heating bag 136 are placed in the heating area for facilitating a heating reaction. Furthermore, in a non-restrictive implementation, air holes 152 may be formed in the bearing seat 138 and the upper cover 150 so as to avoid untight superimposing of grooves in a box body due to steam during heating, and a hole is designed to make the steam generated by heating dispersed from the hole.

In an implementation, the labeling holder 130 is a three-layer type device made of a PP heat-resistant material, namely the tank body 132, the bearing seat 138 and the upper cover 150. The heating bag 136 and a space loading 260 mL of water may be placed in the heating area 134 below the tank body 132. Grooves are formed in side walls of the tank body 132 so that the bearing seat 138 can be supported in the tank body 132. A hole for placing the reaction vial is formed in the bearing seat, such that the frozen crystal reaction vial can be fixed, and a vial bottom is in contact with a box body space for placing the heating bag. Grooves are designed in edges of the upper cover 150 so that the upper cover can be closely combined with a superimposing position of the tank body 132/the bearing seat 138.

Furthermore, the kit of the present invention may further include a 0.22 μm filter. The filter may be a membrane filter available in the market.

In addition, in the heating bag, aluminum powder, calcium oxide, sodium carbonate and sodium hydroxide are mixed proportionally. In a preferred implementation, the heating bag can provide a temperature of at least 95° C. and can maintain the temperature for 14.5 minutes.

The other pattern of the present invention relates to a method for preparing radiopharmaceuticals through the kit. The method of the present invention includes the following steps.

(1) A radioactive nuclide and a buffer solution in a reagent vial are added into a frozen crystal reaction vial, and mixing is performed.

(2) An aqueous solution is added into a heating area to heat up the heating bag.

(3) The frozen crystal reaction vial is placed on a bearing seat to perform a heating reaction, so as to obtain the radiopharmaceuticals.

In an implementation, the peptide pharmaceutical may be DOTATATE, DOTATOC, DOTANOC or DOTAOC. Furthermore, the reagent vial can contain a buffer solution suitable for labeling a specific radioactive nuclide, for example, a 1.5 M sodium acetate/acetate buffer solution (pH 6.0) is configured to label Ga-68, and a 0.3 M ascorbic acid/sodium hydroxide buffer solution (pH 4.3 to 4.7) is configured to label Lu-177. The frozen crystal reaction vial of the present invention can be matched with different reagent vials, so that the kit is not just applicable to labeling a single radioactive nuclide. In the actual using process, a radioactive solution Ga-68 or Lu-177 is added into the frozen crystal reaction vial, and then a solution of the reagent vial is added. Then, water is added into the tank body, and the heating bag in the heating bag is subjected to an exothermic reaction to provide heat energy required in the labeling process. Different from using of a plug-in dry bath heater in the related art, a finished product with a radiochemical purity greater than 95% can be obtained as well.

In an implementation, within 5 minutes after the water is added into the heating bag, the temperature can rise to 95° C. and can be maintained at least for 14.5 minutes.

According to optional implementations of the present invention, a reaction time of performing radioactive nuclide labeling through the kit of the present invention may be at least 5, 6, 7, 8, 9, 10, 11, 12, 13, 14 or 15 minutes. In a specific implementation, when the radioactive nuclide is Ga-68, the reaction time is at least 7 minutes. In another implementation, when the radioactive nuclide is Lu-177, the reaction time is at least 10 minutes. A plurality of embodiments is disclosed below to illustrate various different implementation patterns of the present invention, so that those with general knowledge in the technical field of the present invention can implement the technical content disclosed in the present invention according to the disclosure of the specification. Therefore, the embodiments disclosed below cannot be used to limit the scope of rights of the present invention. Furthermore, all documents cited in the specification are deemed to be fully cited as a part of the specification.

Embodiment 1 Preparation of Labeling Frozen Crystal Reaction Vial and Reagent Vial 1.1 Preparation of Frozen Crystal Reaction Vial A gamete peptide pharmaceutical DOTATATE, DOTATOC, DOTANOC or DOTAOC of a somatostatin type 2 receptor (SSTR2), mannitol and gentisic acid are respectively prepared into solutions with water. The peptide pharmaceutical solution, the mannitol solution and the gentisic acid solution are mixed and filtered to an Ultra inert type I plus vial by a filter membrane with a hole diameter of 0.22 μm. A labeling frozen crystal reaction vial is produced by a freeze dryer and includes 35.7 to 40.5 mcg of the peptide pharmaceutical, 20 mg of the mannitol and 2 mg of the gentisic acid.

1.2 Preparation of Acetate Buffer Solution

An acetate buffer solution is suitable for labeling a radioactive nuclide Ga-68. An acetate solution with a 1.5 molar concentration is taken to be blended with a sodium acetate solution with a 1.5 molar concentration to obtain a sodium acetate mixed solution (with a pH value of 6.0). 0.1 mL of the sodium acetate mixed solution is taken to be mixed with 1.0 mL of hydrochloric acid with a 0.1 equivalent concentration to prepare the acetate buffer solution (with a pH value of 3.0 to 4.0).

1.3 Preparation of Ascorbic Acid Buffer Solution

An ascorbic acid buffer solution is suitable for labeling a radioactive nuclide Lu-177. 50 mg of ascorbic acid and 7.9 mg of sodium hydroxide are taken to be dissolved into 1.0 mL of an aqueous solution to prepare the ascorbic acid buffer solution (with a pH value of 4.3 to 4.7).

Embodiment 2 Preparation of Heating Bag

Figure 3:
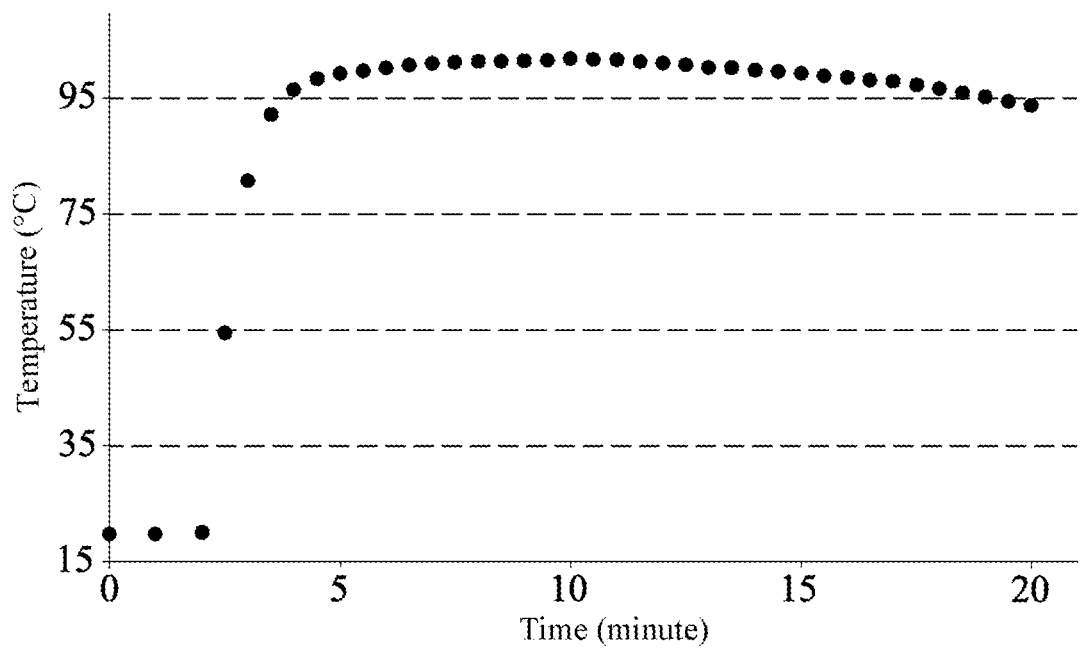
FIG. 3 shows temperature changes in a frozen crystal reaction vial during a labeling reaction according to an implementation of the present invention.

A heating bag is a solid mixture with a net weight of 80 g and includes 15 to 20 wt % of aluminum powder, 50 to 60 wt % of calcium oxide, 20 to 25 wt % of sodium carbonate and 20 to 25 wt % of sodium hydroxide. The heating bag has a dampproof outer bag needing to be removed before using. The heating bag reacts to generate heat energy after 260 mL of normal temperature water is added. A temperature greater than 95° C. required by a reaction for labeling Ga-68 or Lu-177 can be provided, and maintained for at least 14.5 minutes, and a result is shown in FIG. 3.

Embodiment 3 Preparation of Ga-68-DOTATATE Radioactive Injection

Figure 2:
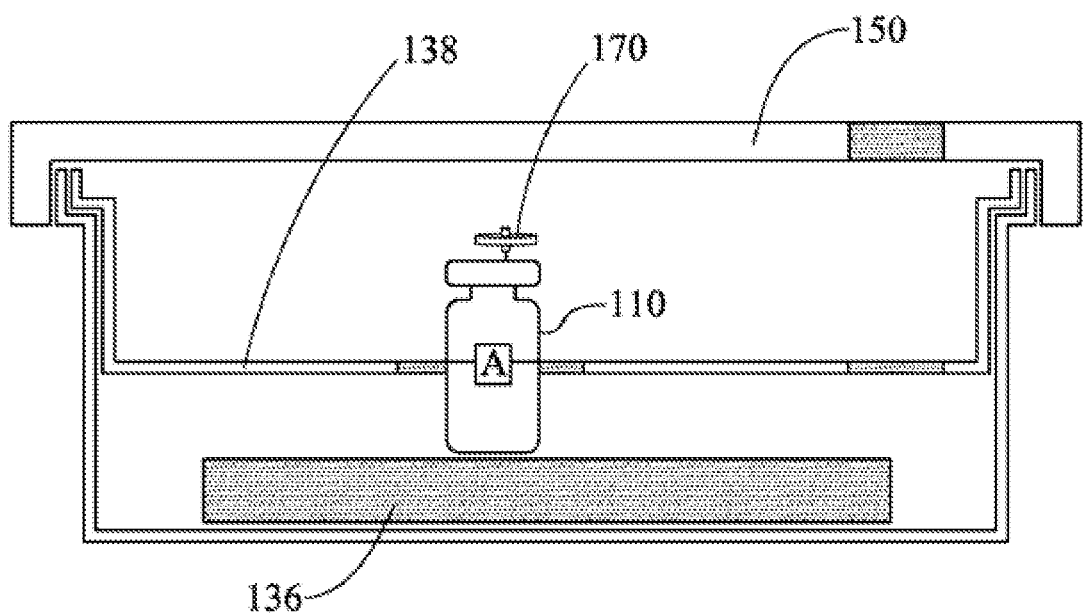
FIG. 2 is a schematic diagram of an actual using manner of the kit for preparing the radiopharmaceuticals.

The present embodiment adopts the kit 100 for preparing the radiopharmaceuticals shown in FIG. 1 for preparation. Reference is made to FIG. 1 and FIG. 2 simultaneously.

Firstly, a Ga-68 solution is washed out from a Ge-68/Ga-68 breeding device produced by Eckert & Ziegler through 5 mL of hydrochloric acid with a 0.1 equivalent concentration. The Ga-68 solution enters a frozen crystal reaction vial 110 through a pipeline. A peptide pharmaceutical in the frozen crystal reaction vial 110 is DOTATATE. Then, 0.5 mL of an acetate buffer solution in a reagent vial 120 is added, and frozen crystals are dissolved and evenly mixed. A 0.22 μm filter 170 is inserted onto the frozen crystal reaction vial 110 for air exhaust. A dampproof package of the heating bag 136 is removed, the heating bag is put into a labeling holder 130, and 260 mL of normal temperature water is added. Then the frozen crystal reaction vial 110 is put onto a bearing seat 138 of the labeling holder 130, the labeling holder is covered with an upper cover 150 of the holder for a labeling reaction, a reaction temperature is 95° C., and a reaction time is 7 minutes.

After the reaction is completed, the frozen crystal reaction vial 110 is taken out. A small quantity of head products are taken for quality control analysis to determine a radiochemical purity, a pH value of a finished product and a radioactive activity. The radiochemical purity is analyzed through an ITLC SG developing sheet and a developing solution prepared from ammonium acetate with a 1 molar concentration and methyl alcohol at a volume ratio of 1:1. The head products are dripped to a position of a developing end of the developing sheet extending in a developing direction by 2 cm, then put into the developing solution by an 8 cm chromatographic length and then metered and read by a thin-layer chromatography. The head products with an Rf value of 0 to 0.1 are uncombined Ga-68 substances. The head products with an Rf value of 0.8 to 1.0 are Ga-68-DOTATATE. The result shows that the radiochemical purity of the Ga-68-DOTATATE prepared according to the method of the present invention is 98.59%, and Rf=0.97.

Embodiment 4 Preparation of Lu-177-DOTATATE Radioactive Injection

The present embodiment adopts the kit 100 for preparing the radiopharmaceuticals shown in FIG. 1 for preparation. Reference is made to FIG. 1 and FIG. 2 simultaneously.

Firstly, Lu-177 non-carrier-added (n.c.a.) is added into a frozen crystal reaction vial 110 through an injection needle. A peptide pharmaceutical in the frozen crystal reaction vial 110 is DOTATATE. Then 1 mL of an ascorbic acid buffer solution (contained by a reagent vial 120) is added, frozen crystals are dissolved and fully mixed, and a 0.22 μm filter 170 is inserted for air exhaust. A dampproof package of a heating bag is removed, the heating bag is put into a labeling holder 130, and 260 mL of normal temperature water is added. Then the frozen crystal reaction vial 110 is put onto a bearing seat 138 of the labeling holder 130, the labeling holder is covered with the upper cover 150 of the holder for a labeling reaction, a reaction temperature is 95° C., and a reaction time is 10 minutes.

After the reaction is completed, the labeling reaction vial is taken out. A small quantity of head products are taken for quality control analysis to determine a radiochemical purity, a pH value of a finished product and a radioactive activity. The radiochemical purity is analyzed through an ITLC SG developing sheet and an EDTA developing solution with a 40 millimolar concentration prepared from a 0.9% normal saline solution. The head products are dripped to a position of a developing end of the developing sheet extending in a developing direction by 2 cm, then put into the developing solution by an 8 cm chromatographic length and then metered and read by a thin-layer chromatography. The head products with an Rf value greater than 1.0 are uncombined Lu-177 substances. The head products with an Rf value of 0.3 to 0.5 are Lu-177-DOTATATE. The result shows that the radiochemical purity of the Lu-177-DOTATATE prepared according to the method of the present invention is 99.99%, and Rf=0.389.

Although the present invention is described with reference to the above embodiments, the embodiments are not intended to limit the present invention. A person of ordinary skill in the art may make variations and modifications without departing from the spirit and scope of the present invention. Therefore, the protection scope of the present invention should be subject to the appended claims.

What is claimed is:

1. A kit for preparing radiopharmaceuticals, comprising:
a frozen crystal reaction vial, comprising a peptide pharmaceutical, gentisic acid and mannitol configured to be mixed with a radioactive nuclide;
a reagent vial, comprising a buffer solution configured to be added into the frozen crystal reaction vial; and
a labeling holder, comprising
a tank body;
a heating area, arranged at a bottom of the tank body;
a heating bag, arranged in the heating area, wherein the heating bag is capable of heating up to at least 95° C. by adding an aqueous solution;

a bearing seat, arranged above the heating area, and configured to bear the frozen crystal reaction vial, and an upper cover, arranged above the tank body wherein the peptide pharmaceutical is DOTATATE, DOTATOC, DOTANOC OR DOTAOC and the radioactive nuclide is Ga-68 or Lu-177.

2. The kit according to claim 1, wherein the heating bag comprises aluminum powder, calcium oxide, sodium carbonate and sodium hydroxide.

3. The kit according to claim 1, wherein the heating bag comprises 15 to 20 wt % of aluminum powder, 50 to 60 wt % of calcium oxide, 20 to 25 wt % of sodium carbonate and 20 to 25 wt % of sodium hydroxide.

4. The kit according to claim 1, wherein at least one air hole is formed in the upper cover.

5. The kit according to claim 1, further comprising a filter, configured to be inserted onto the frozen crystal reaction vial.

6. A method for preparing radiopharmaceuticals through the kit according to claim 1, comprising the following steps:

(1) adding a radioactive nuclide and a buffer solution in a reagent vial into a frozen crystal reaction vial and performing mixing;

(2) adding an aqueous solution into a heating area to heat up a heating bag; and (3) placing the frozen crystal reaction vial on a bearing seat to perform a heating reaction, so as to obtain the radiopharmaceuticals wherein the peptide pharmaceutical is DOTATATE, DOTATOC, DOTANOC OR DOTAOC and the radioactive nuclide is Ga-68 or Lu-177.

7. The method according to claim 6, wherein when the radioactive nuclide is the Ga-68, the buffer solution is an acetate buffer solution.

8. The method according to claim 6, wherein when the radioactive nuclide is the Lu-177, the buffer solution is an ascorbic acid buffer solution.

9. The method according to claim 6, wherein the heating reaction is at a temperature of at least 95° C. for at least 5 minutes.

* * * * *